United States Patent [19]

van Engelshoven

[11] Patent Number: 4,633,718

[45] Date of Patent: Jan. 6, 1987

[54] METHOD AND APPARATUS FOR DETERMINING A STRESS RELAXATION CHARACTERISTIC OF ELASTOMERIC MATERIALS UNDER PRESSURE

[75] Inventor: Ber van Engelshoven, Maastricht, Netherlands

[73] Assignee: Rubber- en Kunststoffabriek ENBI B.V., Nuth, Netherlands

[21] Appl. No.: 858,537

[22] Filed: Apr. 29, 1986

Related U.S. Application Data

[63] Continuation of Ser. No. 711,317, Mar. 13, 1985, abandoned.

[30] Foreign Application Priority Data

Mar. 14, 1984 [DE] Fed. Rep. of Germany ....... 3409252

[51] Int. Cl.$^4$ ............................................. G01N 11/00
[52] U.S. Cl. ....................................................... 73/822
[58] Field of Search ................................... 73/822, 823

[56] References Cited

U.S. PATENT DOCUMENTS

| | | | |
|---|---|---|---|
| 2,482,147 | 9/1949 | Bashore | 73/823 |
| 2,637,203 | 5/1953 | Gehman | 73/823 |
| 2,691,886 | 10/1954 | Cole | 73/823 |
| 2,831,341 | 4/1958 | Chatten et al. | 73/822 |
| 3,807,221 | 4/1974 | Brown et al. | 73/822 |

OTHER PUBLICATIONS

DIN 53,537 (German Industrial Standard Publication), Feb. 1977.

Primary Examiner—Anthony V. Ciarlante
Attorney, Agent, or Firm—W. G. Fasse; D. H. Kane, Jr.

[57] ABSTRACT

A stress relaxation characteristic of an elastomeric material such as rubber and other elastomers under pressure is established by determining the ratio of the difference between two forces acting on a test sample before and after the test sample is stored under compression, to the force acting on the test sample before the sample is stored under compression. First the sample is subjected to an initial deformation, whereby its initial thickness is reduced by 23-27%. Subsequent deformations then amount to not more than 0.05 mm. In order to achieve these quantitatively very small subsequent deformations, the sample is permitted to expand rather than being subjected to additional compressions. Maintaining the exact magnitude of these subsequent deformations in the form of expansions as well as carrying out accurate force measurements is much simpler than causing additional compressive deformations and measuring the respective forces. Furthermore, in the present apparatus, frictional forces, which would disadvantageously affect the measurement values, are eliminated.

12 Claims, 3 Drawing Figures

METHOD AND APPARATUS FOR DETERMINING A STRESS RELAXATION CHARACTERISTIC OF ELASTOMERIC MATERIALS UNDER PRESSURE

This application is a continuation, of application Ser. No. 711,317, filed Mar. 13, 1985 now abandoned.

FIELD OF THE INVENTION

Elastomeric materials such as rubber and other elastomers are used to seal joined pipes, among other items needing a sealing. For sealing pipe joint, a sealing ring of an elastomer such as rubber is held under tension in a collar of a pipe, whereby the sealing ring cross-section is deformed. In order for such a ring to maintain its effective sealing function over a long period of time, it is necessary that the ring material exhibits not only a chemical stability and durability, but also a certain stress relaxation characteristic. It is therefore necessary to test rubber and other elastomers which are to be used for such purposes, by determining the reduction of stress and thus of elasticity in a test sample held at a definite temperature under constant compression. The invention relates to a method and apparatus for carrying out such a test which determines the stress relaxation characteristics of such materials.

DESCRIPTION OF THE PRIOR ART

Methods and apparatuses for determining the stress relaxation of an elastomer test sample are known from the German Industrial Standard Publication (DIN) 53,537. These methods are based on determining the ratio of the difference in the forces acting on a test sample before and after the test sample is stored under compression to the force acting on the test sample initially before it is stored under compression.

For this purpose, first the initial thickness of a test sample is measured at a temperature of 21° to 25° C. to an accuracy of 0.01mm. Then the test sample is subjected within 30 seconds, following the thickness measurement, to an initial deformation compression which reduces the initial thickness of the sample by 23 to 27%. After 10 to 30 minutes the force acting on the sample and causing the initial deformation is measured. The test sample is then stored while the compression is being maintained in order to maintain the initial deformation for a certain length of time. The sample is then subjected to a subsequent deformation which alters the thickness of the sample by 0.05mm at the most. Finally, the force acting on the so deformed sample is again measured within 30 seconds. The second deformation is also a compression deformation.

In the known methods, the sample, which has already been compressed during the initial deformation by 23 to 27% of its initial thickness, is additionally compressed by 0.05mm at the most during the subsequent deformation. The exact determination of the force resulting from the subsequent compression deformation involves practically insurmountable difficulties, as will be shown in the following description of the prior art method.

The test sample which has initially been compressed within 30 seconds by 25±2% of its original thickness must be fixed in this deformed state, which must be maintained throughout the total testing period, except during the subsequent deformation. For this purpose, the test sample is held in a compression apparatus, which comprises a threaded housing and a piston movably mounted in the housing. The deformed state of the test sample is fixed by means of a clamping ring. Both the initial and subsequent deformations of the test sample are arranged within the threaded housing are achieved in that the threaded housing is placed into a tensile testing machine which comprises a compressing linkage including essentially two surface-polished pressure plates which are guided parallel to each other by axial ball bushings. The threaded housing containing the test sample is placed between the parallel pressure plates and may be compressed between them. The separation distance between the two pressure plates may be measured at any time with a dial gage extensometer or micrometer.

Measuring the force by means of this compression testing machine is problematic already after only the initial deformation of the test sample. Difficulties in measuring the force also arise after every subsequent deformation, which are limited to 0.05mm at the most. To avoid these problems it has been suggested to use in addition to electric contacts which indicate when the bottom plate is free, micrometers in order to control for each measurement that the deformation does not exceed 0.05mm. The known electric contacts are, however, too inaccurate to consistently meet this requirement. Furthermore, the contact accuracy is affected by varying atmospheric conditions and other external conditions or effects.

OBJECTS OF THE INVENTION

In view of the foregoing, it is the aim of the invention to achieve the following objects singly or in combination:

to provide a method for determining the stress relaxation of elastomeric materials such as rubber and other elastomers under pressure, in which it is possible not only to achieve a subsequent deformation of a test sample of exactly 0.05mm, but also to cause smaller deformations, as desired, in order to achieve a more exact determination of the stress relaxation under pressure;

to provide such a method which employs an expansion rather than an additional compression, as a subsequent deformation;

to provide such a method wherein the compression force is applied and measured with respect to time, not with respect to distance as in prior art methods, in order to achieve greater accuracy and more evident measured results;

to provide an apparatus to carry out such a method, whereby frictional, torsional, and other external errors which often arise in pistons and locking rings of prior art compression apparatuses, are eliminated from the measured force values;

to provide such an apparatus with a vented ring or annular disk for containing the test sample, in order to avoid air-pillow effect errors, and to allow mediums other than air to be introduced so as to test their effect on the stress relaxation of the sample under pressure; and to make sure that the initial compression and the following expansion of a test sample are exactly defined.

SUMMARY OF THE INVENTION

The above objects have been achieved in a method for determining the stress relaxation of elastomeric materials such as rubber and other elastomers under pressure by determining a ratio of forces and subjecting the test sample to an initial deformation as described above. The present method provides, that the initial deformation load or force is partially relaxed for 10 to 30 minutes to cause a subsequent deformation or rather expansion of not more than 0.05mm at which time the force $K_1$ applied as a result of the relaxation is measured. Then the subsequent deformation or expansion is maintained while the test sample is compression-stored for a specified time period. The term "compression-stored" as used herein, means that the test sample is stored while the reduced compression resulting from said expansion. The sample is then subjected to a second subsequent deformation or rather expansion also amounting to not more than 0.05mm and the force $K_2$ acting on the so deformed sample is again measured within 30 seconds. Hereby, according to the method of the invention, the subsequent deformation of the test sample is a retro- or return-deformation referred to as an expansion whereby the thickness of the sample established by the initial deformation is increased by not more than 0.05mm as a result of the partial relaxation of the initial compression load.

The improvement of the method according to the invention over prior methods is essentially that a subsequent deformation of the already compressed test sample is not achieved by an additional compression, but rather by a retro-deformation or expansion. Not only is such an expanding return deformation quantitatively considerably easier to achieve and to maintain exactly, but it is also achieved without errors in the measured values due to friction effects. Such frictional errors often occur during an additional compression for causing a subsequent or further deformation as is necessary in the prior art.

The method according to the invention is based on the recognition that the magnitude of the difference of forces, acting on a test sample in different states, is independent of the direction of the subsequent deformations relative to the initial deformation. It has been found that the magnitude of the difference between the forces representing the two states is the same for both directions of deformation. In order to determine the stress relaxation of the test sample, the force ratio defined in the German Industrial Standard (DIN) 53,537 can be determined considerably more exactly and more simply by the method according to the invention. The exact magnitude of the retrodeformation or expansion according to the invention may be selected as desired and caused very precisely, quite simply for example by specifying a limit for the rotation in the loosening direction of the locking or clamping sleeve of the present compression apparatus. Thereby, the actual compression force or load on the sample may be instantly determined by reading the measured force, whereby the magnitude of the measured force has not been falsified by any frictional forces.

The method according to the invention may be carried out in a compression apparatus comprising a threaded housing which receives the test sample. The threaded housing comprises a floor plate and a collar forming a pot shaped configuration, holding an axially adjustable clamping sleeve surrounding a compression piston shaft and pressing on a compression plate at one end of the piston shaft for loading a test sample. According to the invention, a spacer ring or annular disk is provided on the floor plate of the housing to encircle the test sample and to limit the extent of the initial deformation by limiting the displacement of the compression piston. The clamping sleeve radially surrounds the shaft of the compression piston with play, and the sleeve may be screwed to rest against an upwardly facing ring surface of the compression plate of the compression piston.

In the apparatus according to the invention, the spacer ring arranged on the floor plate of the threaded housing serves as a piston stroke stop bushing having a height 23 to 27% less than the initial thickness of the test sample, whereby, an exactly limited and hence definite compression is applied to the test sample by the initial deformation in the form of a compression.

BRIEF DESCRIPTION OF THE DRAWINGS

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
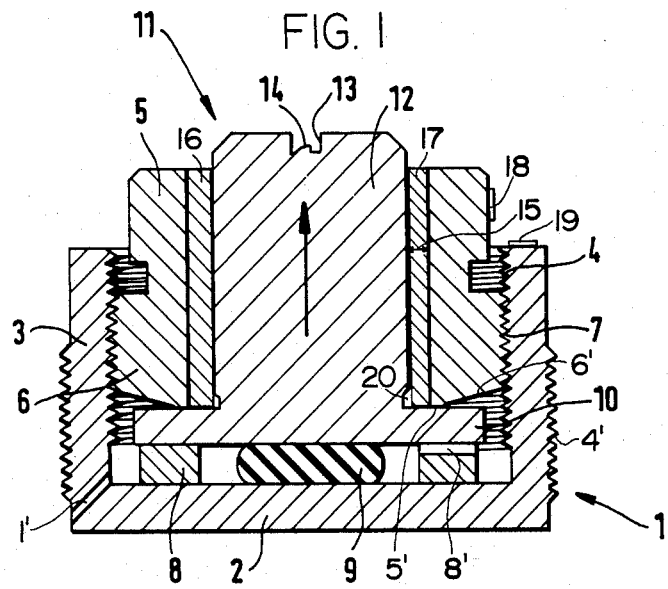
FIG. 1 is a vertical section through an embodiment of a compression and relaxation apparatus according to the invention for carrying out the method according to the invention.

The compression apparatus shown in FIG. 1 comprises a threaded housing 1 having a floor plate 2 provided with a collar 3 forming a pot shaped configuration with an internal threading 4. A clamping sleeve 5 comprises a bulged portion 6 with an external threading 7 which engages the internal threading 4. The housing 1 has an external threading 4' for insertion into a testing stand or the like, not shown.

An annular spacer ring 8 is arranged on the floor plate 2. A test sample 9 is placed within the empty center of the spacer ring 8, for limiting the maximum initial deformation of the sample 9. An initial deformation of the sample 9 is caused by a pressure plate 10 forming the lower end of a compression piston 11. The downwardly facing compression surface of the plate 10 loads the sample 9.

The plate 10 has an upwardly facing ring surface in force transmitting contact with a relatively narrow ring surface 5' of the clamping sleeve 5. For this purpose the bulged portion 6 of the sleeve 5 has a frustum shaped configuration 6'.

The lower ring surface 5' of the clamping sleeve 5 is screwed down against the upper ring surface of the pressure plate 10 for applying an initial deformation to the sample 9. A shaft 12 of the piston 11 extends coaxially through an axial, central bore of the sleeve 5. The outer diameter of the shaft 12 is smaller than the inner diameter of the bore in the locking sleeve 5, so that an annular free play space 15 results between the shaft 12 and the sleeve 5. This free play space 15 is filled for example by two half-cylindrical shim shells 16, 17 during the initial deformation and compressed storage of the sample 9 for preventing a radial movement of the piston 11.

The free end of the piston shaft 12 has a groove 13 in its end face. The groove 13 passes through and extends perpendicularly to the central axis of the piston 11. A spherical segment 14 projects above the floor of the groove 13, coaxially with the central axis of the piston 11. The segment 14 may be a bearing ball set into a hemispherical hole or indentation bored into the floor of the groove 13. The segment 14 assures that any force that may be applied directly to the piston 11 is effective exactly axially on the piston. The groove 13 permits the insertion of a stop member, not shown, for preventing a rotation of the piston, when the clamping sleeve 5 is being rotated. There should also be low friction between the ring surface of the plate 10 and the ring surface 5' of the clamping ring 5.

The annular ring 8 comprises radial openings or passages 8' such as grooves or bores for venting a test chamber enclosed by the plates 2 and 10 and by the ring 8. Further, the housing 1 should also be vented as shown at 1'. By venting the test chamber containing the test sample 9 surrounded by the ring 8 and resting on the floor plate 2, any effects of compressed air in the test chamber are eliminated. A medium may also be introduced through the radial openings 8' into the test chamber during the testing procedure, whereby the effect of the medium on the stress relaxation of the test sample may be determined.

In such an apparatus, the stress relaxation of a test sample 9 may be determined as follows. The sample 9 is enclosed in the compression apparatus which is placed in a testing machine. The initial axial thickness of the sample 9 without compression is first measured. The axial thickness of the spacer ring 8 is 23 to 27% smaller than the initial axial thickness of the test sample 9. An excess- or over-force is axially applied to the piston 11, whereby the sample 9 is compressed within 30 seconds by 25% of the measured initial sample thickness.

During this compression, the piston 11 is supported or braced radially against the clamping sleeve 5 with its thicker portion 6, by means of shim sleeves or half shells 16, 17. Then the clamping sleeve 5 is screwed down against plate 10 of the piston 11, so as to store, so to speak, the compression load to thereby lock or fix the reduced size of the deformed sample 9 in place.

To achieve this initial deformation, a force of, for example, 100N (Newton) is first applied as an excess force, even 50N, for example, would be sufficient force to achieve the initial deformation. This method is possible, because the ring 8, which acts as a displacement stop for the piston 11 takes up the excessive force without being noticeably deformed.

When the locking or clamping sleeve 5 has been tightened down to a locked position, the excess force or load is then removed or discontinued. The shim sleeves 16, 17 which have supported the shaft 12 of the piston 11 may then also be removed.

After a delay time of 10 to 30 minutes, the first measurement is carried out. For this purpose, the excess force is again applied. However, the shim sleeves 16, 17 are now not placed around the pressure piston shaft 12, as they would cause friction errors. When the force of for example 100N, has again been applied, the locking sleeve 5 is screwed looser, so that it moves vertically upwards by 0.05mm for example. A marker 18 and a scale 19 on the sleeve 5 and on the housing collar 3 respectively, or vice versa, aid in the reading of the degree of loosening.

Figure 2:
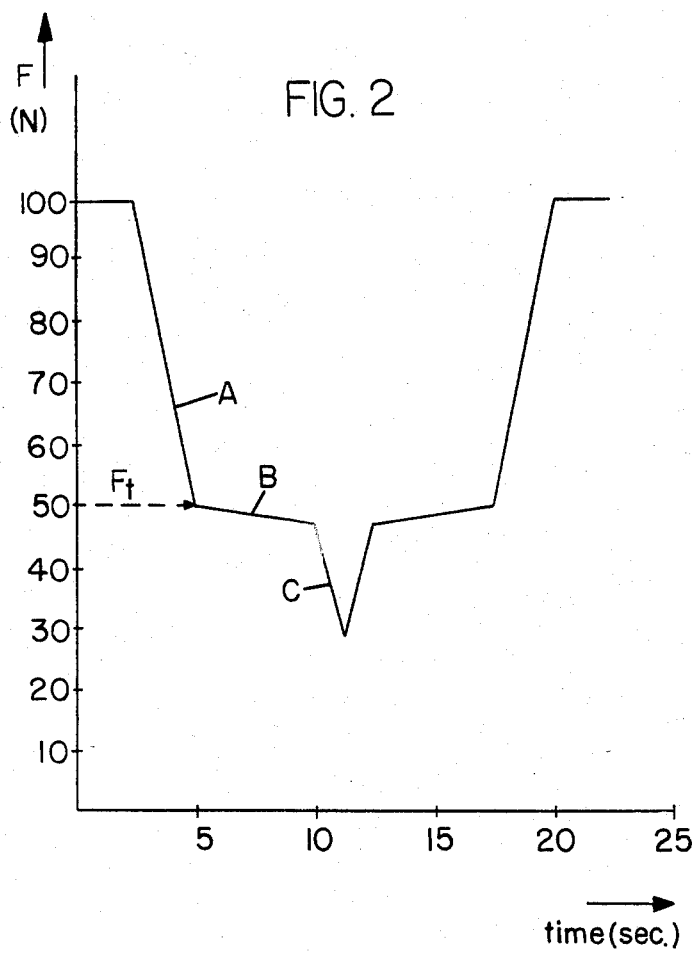
FIG. 2 is a diagram showing the different force or load applications as a function of time $K = f(t)$.

FIG. 2 shows a force-time diagram, $K = f(t)$, illustrating two distinct curve branches for a force reduction. Branch A is relevent as long as a force is still effective on the spacer ring 8. Branch B is relevant from the time on when the force is effective exclusively on the sample 9. During branch A the pressure plate 10 is pushed against the ring 8. During branch B the plate 10 only compresses the sample 9.

If the applied force is reduced to zero over a certain time period, and is then increased over the same time to the initial force value, an essentially V-shaped force-time curve results, as shown in FIG. 2. Each branch of the V-curve is characterized by two clearly recognizable inflextion or kink points. The first branch A of the curve from the starting point to the first kink point represents the removal of the excess force which acts upon the ring 8. The second branch B of the curve between the first and second kink points represents the reduction of force acting only on the sample 9. The branch C of the curve between the second kink point and the zero point represents the decreasing force as the locking sleeve 5 is relieved. When the force is again smoothly increased to the same extent and over the same duration, a second leg results on the forcetime graph, as a mirror image in time and force value of the first curve leg. In contrast, if the force is plotted in a graph as a function of deformation distances rather than time, some parts of the curve would have to represent distances approaching zero, due to the minute deformation distances associated with the steel ring 8 and locking sleeve 5. Therefore, the respective points of change in the curve characteristic may be more easily recognized with a force applied uniformly over time as taught by the invention, rather than over distance.

Furthermore, it is very difficult to make accurate distance measurements of steel parts under load in normal compression test machines. Satisfactory accuracy requires very complicated and costly machines. Therefore, force changes as a function of time are preferred, to carry out the method according to the invention.

Thus, for carrying out the method according to the invention, as described above, an excess force is first applied, and is then reduced over a certain time period, whereby a different force-time curve characteristic is clearly evident for the two time segments when either the excess force or the return deformation force of the sample is being reduced. The testpoint of interest is the first change in the curve characteristic, or the first kink point in the curve. The rest of the curve is, in effect, an automatic cycle back to the initial state, in other words back to the initially applied excess force. Thus, it is sufficient to note only the first two segments of the curve, and otherwise simply to ensure that a complete unloading actually takes place in the first half of the total cycle time, and that the force increases to its initial value of 100N, for example, in the second half of the total cycle time.

The force measurements are preferably repeated four or five times during a compressed storage duration of 168 hours, for example.

After each compressed storage duration, the sample 9 is subjected to a retro-deformation or rather expansion of 0.05mm by means of an appropriate loosening readjustment of the locking sleeve 5, as described above.

Figure 3:
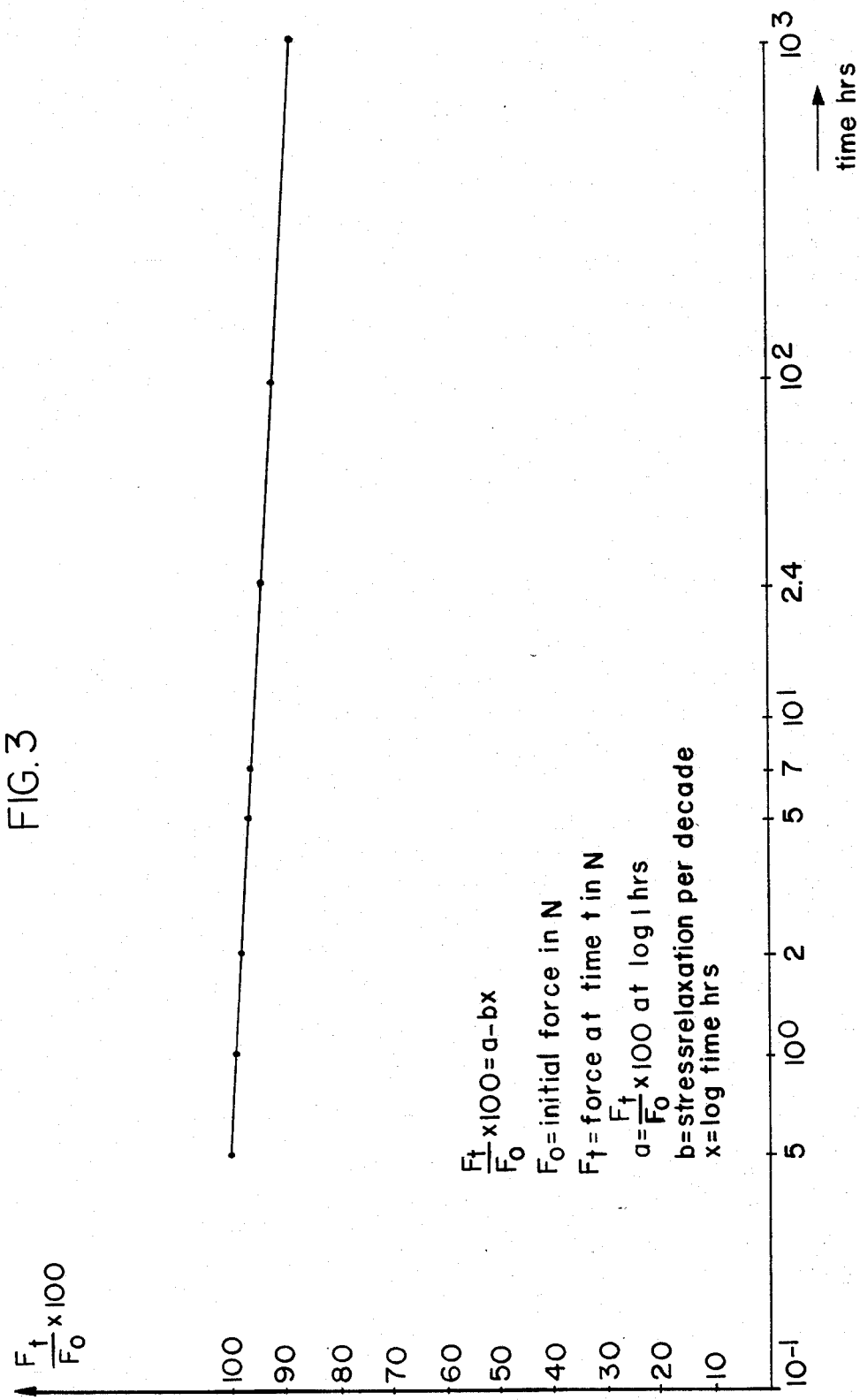
FIG. 3 is a diagram similar to that of FIG. 1 but with a logarithmic time scale to illustrate a test performed over a prolonged time period.

In order to make the relaxation process more apparent, all of the force values measured at various storage duration times are plotted on a single graph, as a function of time which is scaled logarithmically, as shown in FIG. 3.

Incidentally, with respect to FIG. 2 it should be noted that a change in the curve during the first time period is apparent at that point where the plate 10 of the shaft 12 of the piston 11 is lifted off the spacer ring 8.

The subsequently flatter curve is due to the fact that the modulus of elasticity of the steel ring 8 is distinctly different from that of the rubber sample 9.

A further advantage in the method and apparatus according to the invention is seen in that falsely measured values cannot be obtained through any sort of wrong connection or improper operation. In other words, the apparatus allows the method according to the invention to be carried out in a foolproof, error free manner.

Since, in the apparatus according to the invention, the locking sleeve 5 surrounds the shaft 12 of the pressure piston 11 with radial play or free space 15, frictional forces of the locking sleeve on the pressure piston are avoided when the locking sleeve is operated, whereby the resulting force measurement is not falsified by friction forces. If however, an additional compression were required for a subsequent deformation as is necessary in the prior art, a free space or play 15 could not be provided between the locking sleeve 5 and the shaft 12, because an exact guidance of the piston 11 would not be possible with such a play, since the piston could easily deflect or cant sideways while being additionally loaded. In contrast, for a retro-deformation or expansion of the test sample as taught by the invention the pressure piston is not subject to the danger of canting, since it remains held in an exactly vertical position throughout the sample expansion, by means of the upper ring surface of the pressure plate resting against the under ring surface 5' of the locking sleeve 5.

While the known compression apparatus disclosed in the German Industrial Standard Publication (DIN) 53,537 has a threaded housing comprising a lower plate with an external threading, an upper plate with an internal threading, and a pressure disk, an embodiment of the apparatus according to the invention provides that the floor plate of the threaded housing comprises the internally threaded collar 3, and the locking sleeve 5 comprises the externally threaded thicker portion 6. The externally threaded portion can be screwed down to rest axially with its frustum-shaped end against the pressure plate 10 of the pressure piston 11, the shaft 12 of which merges into the plate 10 through a circumferential groove 20, which avoids undesirable stress patterns.

This embodiment of the threaded housing according to the invention is characterized by a very simple construction, whereby the marks 18 and scale 19 may be provided on the collar 3 of the floor plate 2 and on the locking sleeve 5 for indicating the magnitude of any rotation of the locking sleeve 5 with respect to the floor plate 2. The magnitude and direction of rotation are proportional to the magnitude and direction of an axial adjustment of the locking sleeve 5. The reading is greatly facilitated by the magnification provided by the pitch of the threadings 4 and 7 because several degrees of rotation may provide a very small axial displacement. Also, with an appropriate scale, the spacing or distance between the upper surface of the floor plate 2 and the lower surface of the pressure plate 10 may be directly read from the scale.

The shaft 12 of the piston 11 has a smaller diameter than the pressure plate 10 and comprises the groove 13 running perpendicularly through the central axis of the shaft 12, on the end face thereof opposite the pressure plate 10. In this embodiment, it is possible to secure a bar to the surface of the respective pressure plate of a compression testing machine, facing the groove 13 in the end of the piston shaft 12. Such bar engages the groove 13 similar to a screwdriver and when the pressure plate bears down upon the pressure piston 11 the latter cannot rotate when the locking sleeve is rotated. Rotation of the pressure piston must be avoided so that the test sample is not subjected to even a slight torsion load, which would change the respective deformation state.

Preferably, the above mentioned segment 14 forms a dome rising from the floor of the groove in the end face of the piston shaft 12. This dome 14 is centered on the central, longitudinal axis of the pressure piston 11 and would engage a respective central recess in a pressure plate of a compression testing machine not shown. Thus, the line of force can be directed exactly through the central axis of the pressure piston.

Finally, in another embodiment of the apparatus according to the invention, the annular spacer ring 8, which limits the maximum deformation of the test sample 9, comprises at least one groove or bored hole 8' extending entirely through the radial width of the ring 8, for venting, as mentioned above.

This venting is important for preventing the buildup of a pressurized air pillow within the ring or test chamber. Otherwise, an air pillow could falsify the test results. Moreover, the grooves or bores allow any desired medium to be introduced into the test chamber within the ring, to act upon the test sample in its deformed state, in order to determine if, and if so, how the stress relaxation is affected by the medium surrounding the test sample.

It is to be understood that test samples, which have been deformed by means of a compression testing machine, may be removed from the machine together with the compression apparatus which encloses the sample and maintains its deformation, for storing the apparatus with the sample 9 therein for a definite period of time. The compression testing machine may meanwhile be used to prepare other test samples housed in respective other compression apparatuses. Since the shaft of the pressure piston is surrounded with play by the locking sleeve, it may be advantageous to prevent a canting or sideways deviation of the pressure piston of a compression apparatus when it is removed from the compression testing machine. For this purpose the shim sleeves or half-cylindrical shells 16, 17 are inserted between the pressure piston shaft and the locking sleeve, to fill out the free play space 15. Thus, accidental deformations of the sample due to movement or dislocation of the pressure piston 11 are prevented, even if an uncareful handling of the compression apparatus containing the sample should happen. The shim sleeves or shells 16, 17 are also inserted initially to prevent the pressure piston from canting or deflecting sideways during the initial deformation of the sample. The shells 16, 17 are then removed however, to prevent frictional errors in the force measurement as described above.

Although the invention has been described with reference to specific example embodiments, it will be appreciated, that it is intended to cover all modifications and equivalents within the scope of the appended claims.

What I claim is:

1. An apparatus for determining a stress relaxation characteristic of an elastomeric material under pressure, comprising a housing having a base platen and a collar extending from said base plate for forming a pot shaped configuration, having a longitudinal central axis extending perpendicularly to said base plate, a clamping sleeve axially displaceable inside said collar for adjusting the position of said clamping sleeve in said collar in the direction of said central axis, said clamping sleeve having a central bore of given inner diameter, a compression piston having a piston shaft extending through said central bore, said piston shaft having an outer diameter smaller than said inner diameter of said central bore in said clamping sleeve for providing radial play between said piston shaft and said clamping sleeve, said compression piston further having a compression plate extending radially away from said piston shaft, said compression plate having a ring surface in contact with said clamping sleeve and a compression surface for contacting a sample of said elastomeric material resting on said base plate, and a spacer ring resting on said base plate around said sample for contact with said compression surface of said compression piston to limit a stroke of said compression piston when said compression piston deforms said sample.

2. The apparatus of claim 1, wherein said collar has an internal threading and wherein said clamping sleeve has an external threading engaging said internal threading for controlling an axial displacement of said clamping sleeve inside said collar, said clasping sleeve further having a frustum shaped end contacting said ring surface of said compression plate for applying a deformation force to said sample through said compression plate.

3. The apparatus of claim 2, wherein said shaft of said compression piston comprises in its end opposite its compression plate a groove extending perpendicularly to and through said central axis, said groove providing access for a stop means for preventing a rotation of said compression piston.

4. The apparatus of claim 3, wherein said groove has a centrally located spherical segment dome with an axis coinciding with said central axis for a central load application to said compression piston.

5. The apparatus of claim 1, wherein said spacer ring comprises duct means for venting a space enclosed by said base plate, by said compression surface and by said spacer ring.

6. The apparatus of claim 1, further comprising a scale and a marker on said collar and on said clamping sleeve for indicating a relative rotation between said collar and said clamping sleeve.

7. The apparatus of claim 1, further comprising spacer shells for insertion between said piston shaft and said clasping sleeve to prevent a radial displacement of said compression piston.

8. A method for determining a stress relaxation characteristic of an elastomeric material under pressure by determining the ratio $$R = \frac{K_2 - K_2}{K_1}$$

wherein $K_1$ is a force applied to a sample of said elastomeric material after a first storage time and wherein $K_2$ is a force applied to said sample after a further storage time, comprising the following steps:
(a) measuring the starting thickness of said sample at a temperature within the range of 21° C. to 25° C. to an accuracy of 0.01 mm;
(b) applying an initial excess compression load to said test sample for causing such an initial compression of said test sample, that its measured starting thickness is reduced by 23% to 27% to a compressed thickness corresponding to 77% to 73% of said measured starting thickness;
(c) maintaining said initial excess compression load for about 10 to 30 minutes by locking a locking member immediately after applying said initial excess compression load, then causing a first relaxing of said test sample by relieving of said locking member during applying of said initial excess compression load to permit a first partial expansion of said test sample by maximally 0.05 mm and measuring the force $K_1$ effective at the beginning of said first partial expansion of said test sample;
(d) reapplying said initial excess compression load to said test sample, followed by locking said locking member and storing said test sample with the initial excess compression load applied thereto for a predetermined length of time;
(e) after the lapse of said predetermined length of time causing a second relaxing of said test sample to again permit a second expansion of said test sample by maximally 0.05 mm;
(f) measuring of said force $K_2$ effective at the beginning of said second partial expansion of said test sample, whereby the respective ratio R provides an indication of said stress relaxation characteristics; and
(g) repeating said storing and relaxing for measuring further force values $K_2$, whereby each of said repeated relaxing steps permits an expansion of said test sample by maximally 0.05 mm.

9. The method of claim 8, wherein said predetermined length of time of storing said test sample is within the range of about one day to about seven days.

10. The method of claim 9, wherein said repeated relaxing steps with the respective force measurements are perform four to five times within one hundred sixty-eight hours.

11. The method of claim 8, wherein a force representing said initial compression load application and said forces subsequently measured as a result of repeated relaxations are plotted as a function of time.

12. The method of claim 8, wherein said expansion of said test sample of maximally 0.05 mm as a result of a relaxation of the initial load application is measured as a movement of a load application member.

* * * * *

UNITED STATES PATENT AND TRADEMARK OFFICE
CERTIFICATE OF CORRECTION

PATENT NO. : 4,633,718
DATED : January 6, 1987
INVENTOR(S) : Ber van Engelshoven It is certified that error appears in the above-identified patent and that said Letters Patent is hereby corrected as shown below:

Claim 1, Column 8, line 65 (actual line count) replace "platen" by -- plate--;

Claim 2, Column 9, line 24 (actual line count) replace "clasping" by --clamping--;

Claim 7, Column 9, line 49 (actual line count) replace "clasping" by --clamping--;

Claim 8, Column 10, line 1, (actual line count) replace "$R = \frac{K_2 - K_2}{K_1}$" by --$R = \frac{K_1 - K_2}{K_1}$--;

Claim 10, Column 10, line 48 (actual line count) replace "perform" by --performed--.

Signed and Sealed this

Tenth Day of March, 1987

Attest:

DONALD J. QUIGG

Attesting Officer

Commissioner of Patents and Trademarks